(12) United States Patent
Sabliov et al.

(10) Patent No.: US 9,707,185 B2
(45) Date of Patent: Jul. 18, 2017

(54) WATER-SOLUBLE NANOPARTICLES CONTAINING WATER-INSOLUBLE COMPOUNDS

(75) Inventors: Cristina M. Sabliov, Baton Rouge, LA (US); Carlos Ernesto Astete, Baton Rouge, LA (US)

(73) Assignee: Board of Supervisors of Louisana State University And Agricultural and Mechanical College, Baton Rouge, LA (US)

(*) Notice: Subject to any disclaimer, the term of this patent is extended or adjusted under 35 U.S.C. 154(b) by 1375 days.

(21) Appl. No.: 12/596,057

(22) PCT Filed: May 5, 2008

(86) PCT No.: PCT/US2008/062632
§ 371 (c)(1),
(2), (4) Date: Nov. 3, 2009

(87) PCT Pub. No.: WO2008/137831
PCT Pub. Date: Nov. 13, 2008

(65) Prior Publication Data
US 2010/0112073 A1    May 6, 2010

Related U.S. Application Data

(60) Provisional application No. 60/916,387, filed on May 7, 2007.

(51) Int. Cl.
*A61K 9/51* (2006.01)
*A23L 27/00* (2016.01)

(52) U.S. Cl.
CPC ............ *A61K 9/5161* (2013.01); *A23L 27/75* (2016.08); *A61K 9/5123* (2013.01); *Y10S 977/773* (2013.01); *Y10S 977/906* (2013.01)

(58) Field of Classification Search
None
See application file for complete search history.

(56) References Cited

U.S. PATENT DOCUMENTS

| 4,988,679 A | * | 1/1991 | Chavkin | A61K 9/0095 |
| | | | | 514/163 |
| 4,999,205 A | | 3/1991 | Todd, Jr. | 426/250 |

(Continued)

FOREIGN PATENT DOCUMENTS

| JP | 02117610 A | * | 5/1990 | A61K 7/00 |
| JP | 2004-154060 | | 6/2004 | |

(Continued)

OTHER PUBLICATIONS

Hosmani, Carbopol and its Pharmaceutical Significance: A Review, Pharmaceutical Review, 2006, vol. 4, issue 1, printed from http://www.doaj.org/doaj?func=abstract&id=340826, 2 pages, Abstract only.*

(Continued)

*Primary Examiner* — Isaac Shomer
(74) *Attorney, Agent, or Firm* — John H. Runnels

(57) ABSTRACT

Nanoparticles with entrapped, nonpolar compounds are disclosed, and a method for their synthesis. The nanoparticles are readily dissolved or dispersed in water. For example, the entrapped nonpolar compounds may include pharmaceutically-active compounds, or natural colorants. The nanoparticles have a nonpolar compound core, an intermediate surfactant layer, and an outer crosslinked polymeric protective layer. In a prototype example, alginic acid nanoparticles were prepared with beta-carotene entrapped in the core, with lecithin as the intermediate surfactant layer. In an alternative embodiment, a layer-by-layer assembly technique may be used to entrap the colorant within nanoparticles.

18 Claims, 2 Drawing Sheets

(56) References Cited

U.S. PATENT DOCUMENTS

| | | | |
|---|---|---|---|
| 5,478,569 A | 12/1995 | Berneis et al. | 424/456 |
| 5,744,155 A * | 4/1998 | Friedman | A61K 9/0048 424/434 |
| 6,007,856 A | 12/1999 | Cox et al. | 426/250 |
| 6,190,686 B1 | 2/2001 | Isager et al. | 424/439 |
| 6,406,735 B2 | 6/2002 | Stein et al. | 426/540 |
| 6,444,227 B1 | 9/2002 | Leuenberger et al. | 424/489 |
| 6,500,473 B1 | 12/2002 | Koehler et al. | 426/89 |
| 6,635,293 B2 | 10/2003 | Fullmer et al. | 426/250 |
| 6,663,900 B2 | 12/2003 | DeFreitas et al. | 424/492 |
| 7,074,389 B2 * | 7/2006 | Frankenberger et al. | 424/45 |
| 7,081,450 B2 | 7/2006 | Goldshtein | 514/54 |
| 2002/0168334 A1 * | 11/2002 | Jacob | A61K 9/006 424/78.31 |
| 2004/0028745 A1 * | 2/2004 | Bouhadir et al. | 424/488 |
| 2005/0090732 A1 * | 4/2005 | Ivkov | A61N 1/406 600/411 |
| 2005/0202149 A1 | 9/2005 | McClements et al. | 426/601 |
| 2007/0104849 A1 | 5/2007 | McClements et al. | 426/500 |
| 2007/0104866 A1 | 5/2007 | McClements et al. | 427/213.3 |
| 2008/0038552 A1 | 2/2008 | Noack | 428/402 |
| 2008/0044543 A1 | 2/2008 | McClements et al. | 426/573 |

FOREIGN PATENT DOCUMENTS

| | | | |
|---|---|---|---|
| WO | WO 2004 / 060349 | 7/2004 | |
| WO | WO 2005 / 084462 | 9/2005 | |
| WO | WO 2007 / 000193 | 4/2007 | |
| WO | WO 2008063158 A2 * | 5/2008 | A61K 9/5089 |

OTHER PUBLICATIONS

KE Lee, SH Cho, HB Lee, SY Jeong, SH Yuk. "Microencapsulation of lipid nanoparticles containing lipophilic drug." Journal of Microencapsulation, vol. 20 N. 4, Jul.-Aug. 2003, pp. 489-496.*

RH Muller, K Mader, S Gohla. "Solid lipid nanoparticles (SLN) for controlled drug delivery—a review of the state of the art." European Journal of Pharmaceutics and Biopharmaceutics, vol. 50, 2000, pp. 161-177.*

MD Triplett II. "Enabling Solid Lipid Nanoparticle Drug Delivery Technology by Investigating Improved Production Techniques." PhD Dissertation, The Ohio State University, 2004, pages. cover page, pp. i-xv, and pp. 1-172 (188 total sheets).*

Diplomatic Language Services Inc. English Translation of JP 02117610 A. Translation done Nov. 2001. Pages: cover page and pp. 1-14 (15 total sheets).*

Aoki, T. et al., "Influence of environmental stresses on stability of O/W emulsions containing droplets stabilized by multilayered membranes produced by a layer-by-layer electrostatic deposition technique," Food Hydrocolloids, vol. 19, pp. 209-220 (2005).

Astete, C. et al., "Size control of poly(D,L-lacnide-*co*-glycolide) and poly(D,L-lactide-*co*-glycolide)-magnetite Nanoparticles synthesized by emulsion evaporation technique," J. Colloids and Surfaces A, vol. 299, pp. 209-216 (2007).

Astete, C.E. et al., "Synthesis and Characterization of PLGA nanoparticles: A review," J. Biomaterial Science, Polymer Edition, vol. 17, No. 3, pp. 247-289 (2006).

Downham, A. et al., "Colouring our foods in the last and next millennium," International Journal of Food Science and Technology, vol. 35, pp. 5-22 (2000).

Ganea, G. et al., "Experimental Design and Multivariate Analysis for Optimization of Poly (D,L-lactide-*co*-glycolide) (PLGA) Nanoparticle Synthesis Using Molecular Micelles," J. Nanoscience and Nanotechnology, vol. 8, pp. 1-13 (2007).

Klinkesorn, U. et al., "Encapsulation of emulsified tuna oil in two-layered interfacial membranes prepared using electrostatic layer-by-layer deposition," Food Hydrocolloids, vol. 19, pp. 1044-1053 (2005).

Sabliov, C. et al., "Encapsulation and controlled release of antioxidants and vitamins via polymeric nanoparticles," Chapter 12 in N. Garti (Ed.), Delivery and Controlled Release of Bioactives in Foods and Nutraceuticals, Woodhead Publishing Limited (2008).

Zigoneanu, I. et al., "Nanoparaticles with entrapped α-tocopherol: Synthesis, Characterization, and Controlled Release," Nanotechnology, vol. 19, pp. 1-8 (2008).

* cited by examiner

WATER-SOLUBLE NANOPARTICLES CONTAINING WATER-INSOLUBLE COMPOUNDS

This is the United States national stage of international application PCT/US2008/062632, international filing date 05 May 2008, which claims the benefit of the 07 May 2007 filing date of U.S. provisional patent application 60/916,387 under 35 U.S.C. §119(e).

TECHNICAL FIELD

This invention pertains to water-soluble or water-dispersible nanoparticles that incorporate water-insoluble nonpolar compounds, such as nonpolar colorants or nonpolar pharmaceutical compounds.

BACKGROUND ART

Colorants are important components of food. Color affects consumer perception of food quality. Synthetic colorants are often used to impart color. Strict regulatory requirements make it difficult to obtain approval for new synthetic colorants. There is an unfilled need for a greater number of natural foods that incorporate natural colorants. A major obstacle is that many natural colorants are insoluble in water. Examples of water-insoluble, nonpolar natural colorants include the carotenoids and xanthophylls; many of these compounds are also believed to have beneficial health effects. The use of natural pigments has generally been restricted to hydrophobic environments. Water-based products have primarily used synthetic water-soluble colorants. Perceived health issues associated with synthetic colorants have triggered colorants. Perceived health issues associated with synthetic colorants have triggered an increased interest in natural colorants (pigments) suitable for use in foods. Prior approaches to incorporating lipophilic natural molecules in water-dispersible systems have included vehicles such as liposomes, vesicles, microparticles, and emulsions.

Many natural colorants, such as beta-carotene and curcumin, have not been well-suited for use in water-based food systems. Their low water solubility leads to non-uniform color distribution in the food, which is generally unacceptable to consumers. Many are also subject to oxidative degradation.

In the food industry, carotenoid colorants have primarily been used in hydrophobic environments. They have also been used in a limited number of emulsions and protein complexes in water-based foods. Carotenoids are widely distributed in nature. Natural annual production has been estimated at ~$10^8$ ton/year of carotenoids, with a high percentage of that total from marine algae and green leaves. Other sources include peppers, saffron, red palm oil, and turmeric. Carotenoids are often found in free form in leaves, and esterified in other tissues. Carotenoids that have been approved by FDA for use as color additives include bixin and norbixin from annatto seeds, capsanthin and capsorubin from paprika extracts, and β-carotene from micro-algae or synthetic sources.

The European Union allows chlorophylls to be used as colorants. Chlorophyll, the compound primarily responsible for photosynthesis, is found in green plants, green algae, and cyanobacteria. Chlorophyll is a cyclic tetrapyrrole, with a magnesium atom coordinated in the center. Chlorophyll is typically is extracted with organic solvents. The thermal lability of the coordinated magnesium affects color stability, limiting chlorophyll's use as a colorant. Copper chlorophyllins, formed by chlorophyll saponification, are more stable and more water-soluble; copper is not as easily displaced as magnesium. Copper chlorophyllins are approved for use as colorants in the United States. They are typically prepared as a sodium or potassium salt, and tend to precipitate at low pH.

Curcumin is extracted from the rhizome of turmeric plant. It is yellow, soluble in nonpolar solvents, but almost insoluble in water at pH below 7. In alkaline pH the yellow color shifts to red and brown-red. Curcumin color is affected by light, temperature, oxygen, and the presence of metal ions, particularly when not protected by a lipophilic environment, for example when stored as a dry powder. Food-grade polysorbate 80 has been used as a surfactant or emulsifier for curcumin in water-based food products. Curcumin is less expensive than lutein, with similar greenish-yellow shades, but is more susceptible to photo-bleaching.

Anthocyanins are glycosides of anthocyanidins and sugars. Anthocyanins are water-soluble when a net charge is present. The most abundant natural source for anthocyanins is grape pomace, a byproduct of wine production. They have a range of colors, with higher levels of hydroxyl groups giving a more bluish color, and higher levels of methoxy a more reddish color. Likewise, color is affected by pH, typically ranging from purple-red at pH 3, to nearly colorless at pH 5, to blue or even green at a neutral or alkaline pH.

Emulsions have sometimes been used to make water soluble systems from lipophilic natural pigments. Surfactants (such as those in the polysorbitol family) are used to incorporate an oily natural pigment into micelles. They sometimes include stabilizing agents (e.g. antioxidants, anti-foaming agents). However, such emulsions tend to be subject to phase separation.

There is an unfilled need for improved techniques to disperse lipophilic natural pigments and other nonpolar compounds in water, in a manner that provides good stability against oxidative degradation and photodegradation, and that is subject to minimal if any phase separation of the lipophilic compound from the water soluble matrix, over a reasonable range of pH and temperature.

A. Downham et al., "Colouring our foods in the last and next millennium," *International Journal of Food Science and Technology*, vol. 35, pp. 5-22 (2000) is a recent review article, describing the history of food coloring, and the status of available colorants.

U. Klinkesorn et al., "Encapsulation of emulsified tuna oil in two-layered interfacial membranes prepared using electrostatic layer-by-layer deposition," *Food Hydrocolloids*, vol. 19, pp. 1044-1053 (2005) discloses tuna oil-in-water emulsions stabilized with lecithin-chitosan membranes prepared as layer-by-layer electrostatic deposition. The initial tuna oil-in-water emulsion was prepared by placing tuna oil directly in a high-speed blender with an aqueous, buffered solution of lecithin; followed by passage through a high-pressure valve homogenizer. Particle diameters were reported at least as small as 260±10 nm.

T. Aoki et al., "Influence of environmental stresses on stability of O/W emulsions containing droplets stabilized by multilayered membranes produced by a layer-by-layer electrostatic deposition technique, *Food Hydrocolloids*, vol. 19, pp. 209-220 (2005) discloses corn oil-in-water emulsions stabilized with sodium dodecyl sulfate-chitosan-pectin membranes prepared as layer-by-layer electrostatic deposition. The initial corn oil-in-water emulsion was prepared by corn oil directly in a high-speed blender with an aqueous, buffered solution of sodium dodecyl sulfate; followed by passage through a high-pressure valve homogenizer. Particle diameters were reported at least as small as 270±30 nm.

See also published U.S. patent applications 2005/0202149, 2007/0104849, 2007/0104866, and 2008/0044543.

U.S. Pat. No. 6,635,293 discloses an emulsion in which the aqueous phase contained an emulsifier, such as a sucrose fatty acid ester or a polyglycol ester, and an antifoaming agent. Carotenoids were mixed into the aqueous phase to form a stable emulsion. It was said that no elevated temperatures, high-shear mixing, or organic solvents were required to form the product, except that some ethanol might be added to reduce viscosity. The emulsion was a viscous liquid that could be used directly as an emulsion, or converted to freeze-dried form.

Other formulations have been based on colloids such as gelatins, including pork, cow, and fish gelatins. For example, U.S. Pat. No. 5,478,569 describes water-dispersible preparations of fat-soluble compounds, such as beta carotene, using fish gelatin as a hydrocolloid.

U.S. Pat. No. 6,007,856 describes oil-in-water dispersions of beta-carotene and other carotenoids that were said to be stable against oxidation. The oil-in-water dispersions are prepared from a water-dispersible beadlet containing a colloidal carotenoid, where the carotenoid is released from the beadlet and is in intimate contact with sufficient oil phase such that the carotenoid is stabilized against oxidation in the presence of the water phase. The beadlet is formed by dissolving the carotenoid in a water-miscible organic solvent (or dissolved in oil with heating), mixed with an aqueous solution of a swellable colloid (typically gelatin), precipitated in a colloidally dispersed form and then dried to form a colloidal dispersion or beadlet.

U.S. Pat. No. 6,444,227 discloses a process for preparing beadlets containing fat-soluble substances by forming an aqueous emulsion of a fat soluble substance, a gelatin, and a reducing agent; optionally adding a crosslinking enzyme; converting the emulsion into a dry powder; and crosslinking the gelatin matrix in the coated particles by exposing the coated particles to radiation or, if a crosslinking enzyme is present, by incubating the coated particles.

U.S. Pat. No. 6,406,735 discloses a process for making a pulverous preparation having a finely divided carotenoid, retinoid or natural colorant, which process comprises the steps of: a) forming a suspension of the active ingredient in a water-immiscible organic solvent; b) feeding the suspension to a heat exchanger; c) heating the suspension to 100-250° C., with a residence time in the heat exchanger less than 5 sec to provide a solution; d) rapidly mixing the solution of step c) with an aqueous solution of a swellable colloid so that the resulting mixture has a temperature 20-100° C.; e) removing the organic solvent; and f) converting the dispersion of step e) into a pulverous preparation.

U.S. Pat. No. 6,190,686 discloses water-dispersible compositions containing a hydrophobic pigment such as a carotenoid, curcumin, porphyrin pigment, or vegetable carbon. The pigments were dispersed in the aqueous phase, without a surfactant, using a hydrocolloid such as gelatin, milk protein, xanthan gum, agar, alginate, carrageenan, pectin, starch derivatives, dextran, or carboxymethyl cellulose.

U.S. Pat. No. 6,500,473 discloses the use of pectin to entrap natural pigments. Pectin having a high degree of acetylation was reported to protect natural pigments against degradation. Examples of natural pectins with a high degree of acetylation include beet, chicory, and Jerusalem artichoke.

U.S. Pat. No. 6,663,900 discloses a method of forming carotenoid microcapsules with a mixture of hydrocolloids. Crystalline carotenoid was processed in a fluidized bed coating machine, with a protective coating applied such as a sugar or sorbitol, a starch or maltodextrin, and optionally a coating protein such as gelatin.

U.S. Pat. No. 4,999,205 discloses a method of forming a complex between the natural colorant curcumin and a water-soluble polysaccharide or protein (e.g., gelatin) by reacting an aqueous alkaline solution of curcumin with the substrate in water, followed by neutralization to complex the curcumin to the substrate.

See also the following work by us and our colleagues: I. Zigoneanu et al., "Tocopherol encapsulated PLGA nanoparticles: Synthesis, Characterization and Stability," *Nanotechnology*, vol. 19, p. 105606 (2008); G. Ganea et al., "Use of Experimental Design and Multivariate Analysis for Optimization of Poly (D,L-lactide-co-glycolide) (PLGA) Nanoparticle Synthesis Using Molecular Micelles," *J. Nanoscience and Nanotechnology* (in press 2008); C. Astete et al., "Size Control of Poly(D,L-Lactide-co-Glycolide) and Poly(D,L-Lactide-co-Glycolide)-Magnetite Nanoparticles Synthesized by Emulsion Evaporation Technique," *J. Colloids and Surfaces A*, vol. 299, pp. 209-216 (2007); C. Astete at al., "Synthesis and Characterization of PLGA nanoparticles: A review," *J. Biomaterial Science, Polymer Edition*, vol. 17, pp. 247-289 (2006); and C. Sabliov et al., "Encapsulation and controlled release of antioxidants and vitamins via polymeric nanoparticles," Chapter 17 in N. Garti (Ed.), *Controlled Release Technologies for Targeted Nutrition* (2008, in press).

There is an unfilled need for improved systems to solubilize lipophilic compounds, such as natural colorants, in water—systems that are stable (with minimum phase separation, precipitation, and oxidation), that employ natural products, that impart an uniform color or other uniformly dispersed properties in water, that are not overly sensitive to changes in temperature and other parameters, that are reproducible (batch by batch), scalable, and inexpensive.

DISCLOSURE OF THE INVENTION

We have discovered water-soluble or water-dispersible polymeric nanoparticles with entrapped nonpolar compounds that are otherwise insoluble in water, and a method for their synthesis. For example, the entrapped nonpolar compounds can include pharmaceutically-active compounds, or natural colorants such as natural lipophilic carotenes, which are useful for example in food products and other uses where natural colorants or other properties of natural compounds are desirable. Other uses include delivery of flavoring agents, nutritional components, preservatives, and other lipids or lipid-soluble compounds.

In a prototype example, we prepared alginic acid nanoparticles with entrapped beta-carotene cores, in the presence of lecithin surfactant. The natural alginic acid polymer is a polysaccharide having a random distribution of beta-D-mannuronic acid and alpha-L-guluronic acid units. It is produced by several microalgae. It is used in the food industry as a thickening agent and as an emulsifier. The surfactant lecithin is a phospholipid with two hydrocarbon tails and a polar head containing charged phosphate and amine groups. Lecithin is a well-tolerated, non-toxic surfactant. The colorant beta-carotene is naturally present in many fruits and vegetables. In the prototype synthesis, beta-carotene was dissolved in ethyl acetate. The organic solution was added to an aqueous phase with dissolved lecithin and calcium chloride. The resulting emulsion was sonicated to reduce the size of the emulsion droplets or micelles. The sonicated emulsion droplets comprised an oily core of beta-carotene in ethyl acetate, stabilized by an outer lecithin layer. Next, $CaCl_2$ was added to the emulsion slowly, with stirring. The sonicated emulsion droplets were then covered with an alginic acid layer, formed by adding the emulsion with $CaCl_2$ to an alginic acid solution with additional sonication. The calcium acts to crosslink alginate molecules in the outer layer of the nanoparticles to one another, or to crosslink alginate and lecithin molecules. The solvent was removed by evaporation under reduced pressure. The final product was a stable, yellow-orange suspension that was completely water soluble. No phase separation, precipitation, or color change was observed after a period of several weeks, depending on the nanoparticle size and the solvent used. (Precipitation was more prevalent when chloroform was used as the solvent than when ethyl acetate was used. Precipitation also tended to occur more readily as the particle size increased.)

In a preferred embodiment, the natural colorant is entrapped without chemical modification of the natural pigment, all components of the nanoparticles are GRAS substances, the resulting system imparts a uniform color to a water-based composition such as a food product, different color hues may be obtained at different dilutions of the particles, and the system is stable over a period of time.

In an alternative embodiment, a layer-by-layer assembly technique may be used to entrap the colorant within nanoparticles, using an organic (non-polar) solvent. The use of the nonpolar solvent allows the formation of smaller particles than has been reported for prior techniques.

MODES FOR CARRYING OUT THE INVENTION

Figure 1:
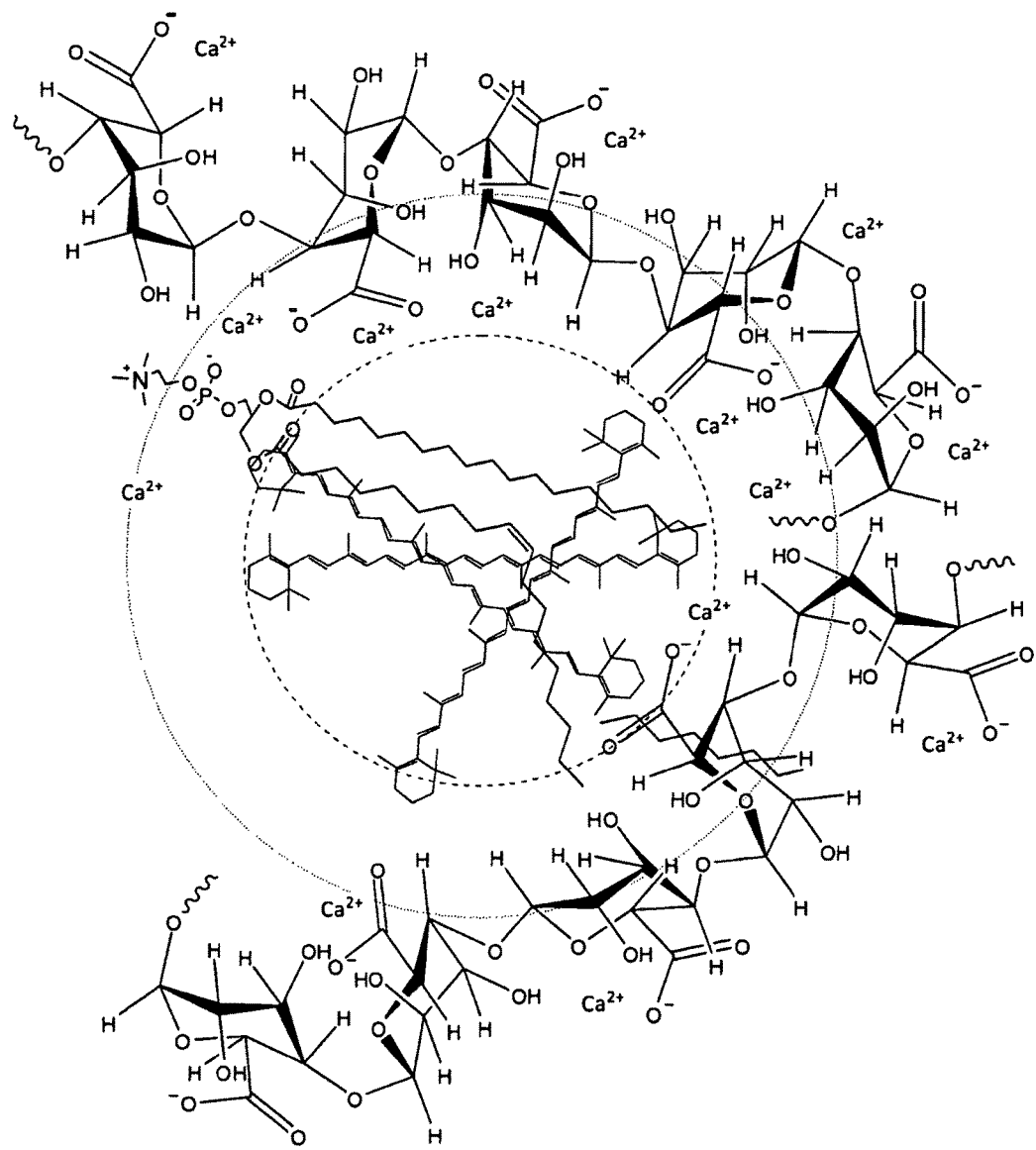
FIG. 1 depicts schematically one embodiment of a nanoparticle in accordance with the present invention.
Figure 2:
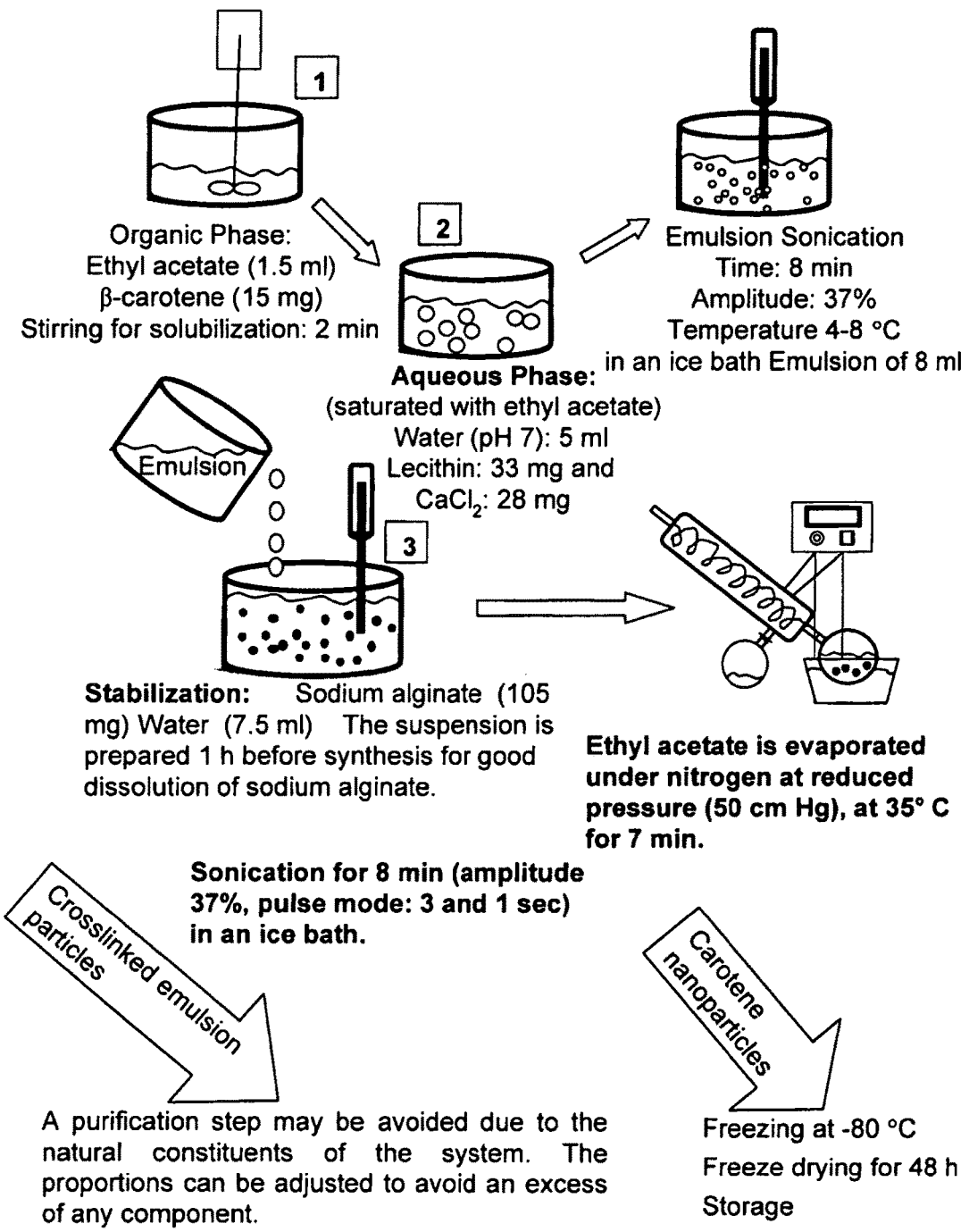
FIG. 2 depicts schematically one embodiment of a process for synthesizing nanoparticles in accordance with the present invention.

Water-soluble nanoparticles that incorporate entrapped, water-insoluble colorants (i.e. carotenoids, xanthophylls) may be used, for example, to impart color to water-based foods, such as juices, pasta, snacks, deserts, etc. The nanoparticles may be used in other industries to impart color as well, e.g., to cosmetics and health care products. In a preferred embodiment, especially when used as a food coloring, all components of the nanoparticles are themselves natural GRAS components: colorant, polymer, and surfactant; although this is not required.

The novel nanoparticles may also be used to encapsulate compounds for other uses, for example to increase the viscosity of foods or other products, to protect and deliver bioactive or diagnostic components (e.g., vitamins, antioxidants, antifungals, antibacterials, antivirals, magnetic materials, pharmaceutical compounds, etc.), with applications in disease treatment and diagnosis. As one example, they can be particularly useful for delivering drugs for treating diseases of the colon.

The novel method may be used to stably encapsulate natural colorants in polymeric nanoparticles as an effective way to improve dispersion in water, and to produce a homogenous color, without altering a food's consistency or taste. For example, beta-carotene may be used to impart a homogeneous yellow-orange color to foods. An additional benefit of natural coloring agents is their antioxidant properties, which have been linked with prevention of several diseases, such as atherosclerosis, cancer, and cardiovascular and neurodegenerative diseases. These beneficial functional properties are maintained by the novel encapsulation method.

Nanoparticle synthesis. The nonpolar, water-insoluble compound, (e.g., a natural colorant, or mixture of colorants, or pharmaceutically-active compound or compounds) is dissolved in an organic solvent, preferably at room temperature. If desired, the color hue can be modified by using different concentrations of individual colorants, or mixtures of different colorants. The color hue and color distribution in water may also be adjusted by altering the ratios of colorant: surfactant:polymer. An emulsion is formed by mixing the organic phase into an aqueous phase containing a surfactant. The emulsion is then microfluidized (or sonicated) to reduce the size of the emulsion droplets. The emulsion is then mixed with a polymer solution (e.g., alginic acid), in the presence of a cross-linking agent (e.g., divalent ions such as calcium or magnesium). The organic solvent is evaporated, and the nanoparticle suspension is collected. The suspension may be stored in liquid form for characterization or further use. Alternatively, the nanoparticle suspension may be lyophilized or spray-dried to form a powder. In the prototype experiments described below, particle sizes were reduced by sonication, and freeze-drying was used to dry the nanoparticle suspensions. Alternatively, sonication could be replaced with microfluidization, and freeze-drying with spray-drying.

Nanoparticle characterization. The nanoparticles are characterized by morphology (SEM), size, size distribution (DLS), color (L, a, b), and stability. Stability is determined for nanoparticles in both suspended and dried forms, with respect to processing conditions, including temperature, and pH, and storage time. For comparison, tests are conducted both with laboratory-grade chemical components and food-grade components; the latter may sometimes be less pure, but will generally be less expensive.

In a preferred embodiment, only natural components are used in preparing the nanoparticles of this invention, particularly "GRAS" components (generally recognized as safe). Also, care should be taken to ensure that the organic solvent used is eliminated to the level required by FDA or other applicable regulations.

In a prototype embodiment, β-carotene was used as the colorant, lecithin as the surfactant, alginic acid as a hydrocolloid-forming polymer, and ethyl acetate was used as the solvent. We have entrapped from 0.1% to 10% (w/w) β-carotene in the nanoparticles, and we expect that this fraction could readily be increased to at least ~20% (w/w).

Ethyl acetate is a GRAS solvent, but it should still be essentially completely eliminated from the final product. Its water solubility is low, so the water phase is saturated with ethyl acetate to inhibit ethyl acetate diffusion into the aqueous phase during emulsification and nanoparticle synthesis. Other organic solvents may also be used such as ethanol or acetone; however, these two solvents are completely miscible with water, so the mechanism of organic phase formation during emulsification will be different from that for a truly immiscible phase, and lower entrapment efficiency of the hydrophobic component (e.g., colorant) should be expected.

Lecithin is a natural surfactant. Its choline group contains both positive and negative charges. Lecithin is unique among GRAS surfactants in that it is electrostatically charged, allowing it to interact with oppositely charged biopolymers in aqueous solution. As a surfactant, the lecithin molecules will tend to form micelles, positioning themselves at interfaces between the nonpolar solvent and water. The hydrocarbon chains are oriented toward the organic phase, and the hydrophilic choline is directed to the aqueous phase. The positive outer charges facilitate interaction with negatively-charged groups in alginic acid, leading to the deposition of alginic acid molecules onto the surface of the micelles. The alginic acid then forms a protective shell around the core.

The negative charges in the alginic acid molecules permit crosslinking in the presence of divalent cations such as calcium and magnesium. The concentration of the alginic acid (or other hydrocolloid-forming polymer) affects the thickness of the polymer layer and inter-particle interactions; a thicker polymer layer will generally result in larger particles having higher polydispersity. Alginic acid is preferred over sodium alginate, because the former has a higher density of negative charges. Alginic acid dissolves well in a slightly basic, aqueous solution (e.g., pH ~8).

A crosslinking step helps stabilize the nanoparticles. Calcium chloride is a preferred crosslinking agent; other sources of calcium, or other divalent cations such as magnesium may also be used. Calcium ions can bind to negatively-charged moieties from different alginic acid chains; the crosslinked alginic acid will confer a more compact barrier to reduce the diffusion of compounds from the core to the exterior of the nanoparticles. The crosslinking helps to preserve a more stable hue overtime, to inhibit degradation of the natural pigments, to inhibit mechanical degradation of the particles, and to reduce potential interactions with other food components. The solution of calcium chloride should be added in a way that minimizes both potential inter-particle interactions, as well as potential intramolecular interactions. The calcium should not be added to the first aqueous solution prior to emulsification, because it can interact with lecithin, interfering with emulsion formation. Premature interaction between calcium ions and lecithin can result in a complete phase separation when the organic phase is added, because there can then be insufficient free surfactant. It is therefore strongly preferred to add calcium after the emulsification step. Furthermore, our experimental results suggested that higher levels of particle aggregation can occur at higher concentrations of alginic acid and higher concentrations of $CaCl_2$ (data not shown). Thus it is preferred that the concentration of neither the polymer nor the crosslinking agent be so high that they promote substantial levels of particle aggregation.

The particles are more stable against oxidative degradation in long-term storage in dried form, rather than suspension. It is preferred that the particles be stored in an inert atmosphere (e.g., nitrogen) to inhibit oxidation. If microbial degradation is a concern, antimicrobial agents may optionally be added.

EXAMPLE 1

Carotene dissolution. The active component, 10 mg β-carotene, was weighed and placed in a 10 ml round cap bottle. The solvent, 10 ml ethyl acetate was then added to the bottle with a pipette to dissolve the carotene. The dissolution occurred in seconds at room temperature with manual shaking.

EXAMPLE 2

Emulsification. Nanopure water (10 mL) was saturated with ethyl acetate in a separatory funnel. (Nanopure water was used in these examples to avoid contamination with dust or bacteria, that might have led in turn to errors in the measurements of particle size. However, in general it is not necessary to use nanopure water in practicing this invention.) The ethyl acetate-saturated water was transferred to a 20 mL vial, along with 28 mg (50.5 mM) $CaCl_2$, and 200 mg lecithin (i.e., phosphatidylcholine). The mixture was stirred for 5 min with a magnetic stirrer, with the vial's cap secured to inhibit solvent evaporation. The carotene solution (organic phase) was added to the second solution (aqueous phase), and the mixture was sonicated for 8 min (amplitude 37%, pulse mode: 3 sec on and 2 sec off) in an ice bath to maintain the temperature below 10° C. The sonicator used was a probe-type sonicator set at 750 W; typical operating parameters for sonicating a 15 mL sample were sonication for a period of 10 minutes under the conditions described above, with a "10-100 mL" tip, for a total energy received on the order of 9 kJ.

EXAMPLE 3

Stabilization

| | |
|---|---|
| Aqueous phase = nanopure water | 7.5 ml |
| Polymer = alginate | 75 mg |

Alginic acid (105 mg) was completely suspended in 7.5 ml nanopure water by constant magnetic stirring in a 50 ml beaker for one hour before reaction with the emulsion. The emulsion was added to the alginic acid aqueous suspension with a syringe or pipette. The mixture was sonicated for 8 min (amplitude 37%, pulse mode: 3 sec on, 1 sec off). After sonication, the suspension had a highly uniform, red color. The suspension was placed in a round bottom evaporator flask to remove the ethyl acetate solvent under nitrogen at reduced pressure (7 min, 50 mm Hg pressure, temperature 35° C.). The final suspension product showed an intense orange-red color, with no visible evidence of phase separation. The product may be stored in liquid form. Alternatively, if a powdered form is preferred, the liquid suspension may be lyophilized or spray-dried.

EXAMPLE 4

Comparative color photographs. Color photographs do not reproduce well in typical patent publications, and are therefore none are presented here. However, on page 8 of the priority application (U.S. provisional application 60/916, 387) appear two color photographs that compare a suspension of the polymeric nanoparticles with entrapped β-carotene, prepared as described above, with unmodified β-carotene dispersed in water. Electronic (PDF) copies of the priority application, including these photographs, will be accessible by the public through the websites of the United States Patent and Trademark Office, and of the World Intellectual Property Organization, after the present application has been published. The photographs clearly depict the non-uniform color and distribution that were observed with the unmodified, poorly soluble β-carotene in water (left), versus the uniform red color obtained with the novel, soluble, β-carotene nanoparticles in water (right).

EXAMPLE 5

Particle Size. Transmission electron microscopy (TEM) images (not shown) of the β-carotene nanoparticles showed particles having a spherical shape and diameters in the 700 nanometer range. The size depended upon a number of factors, particularly the identity of the solvent that was used. The size and size distribution were further evaluated by dynamic light scattering (DLS).

With $CaCl_2$ concentration held constant at 0.15 mg/mL, the particle size was significantly and substantially smaller when chloroform was used as the organic solvent than when ethyl acetate was used. The particle size ranged from 500 to 950 nm for alginic acid concentrations of 0.07 to 3.5 mg/ml when ethyl acetate was the organic solvent, compared to 120 to 220 nm when chloroform was used at the same alginic acid concentrations. For both solvents, average particle size increased as the alginic acid concentration increased.

The difference in particle size was attributed to β-carotene solubility in the two solvents. β-carotene is soluble in chloroform at concentrations up to 20 mg/ml, compared to only 0.5 mg/ml in ethyl acetate. Based on these results, we hypothesize that smaller cores will generally result where the colorant (or other encapsulated compound) has a higher solubility in the organic solvent used, and larger cores where that solubility is lower.

EXAMPLE 6

Particle Size Distribution. Particle size distributions were measured by dynamic light scattering. A polydispersity index ("PI") lower than about 0.1 is typically considered to represent a relatively monodisperse particle size distribution. The particles that were synthesized with ethyl acetate had a significantly higher PI, with values ranging from 0.5 to 0.65. When chloroform was used as the organic solvent, PI values ranged from 0.4 to 0.55. Based on these results, we hypothesize that a more uniform particle size distribution will generally result where the colorant (or other encapsulated compound) has a higher solubility in the organic solvent used, and a broader distribution where that solubility is lower.

EXAMPLE 7

Precipitation/persistence of colloidal suspension. The larger particles synthesized with ethyl acetate tended to precipitate more readily from an aqueous system, while the smaller particles synthesized with a chloroform solvent stayed in suspension. The particles that had been synthesized with ethyl acetate precipitated in a matter of hours. Precipitation after 6 hours was noticeable, and was pronounced by 24 hours. The color of the suspension changed as a function of time due to precipitation, from orange-red to transparent red. By contrast, the particles synthesized with chloroform showed no visible precipitation after 24 hours, due to the smaller particle size. Different colors could be obtained in the suspension with the chloroform-prepared particles by varying the dilution, from red to orange at higher concentrations, and orange to yellow at lower concentrations. Based on these results, chloroform is a preferred solvent in the synthesis of β-carotene nanoparticles. More generally, the preferred solvent will be one that produces smaller particles sizes, which we expect will usually correlate with higher solubility of the particular compound in the solvent.

EXAMPLE 8

Particle morphology. Particle morphology was studied by transmission (TEM) and scanning (SEM) electron microscopy (data not shown). Particles synthesized without calcium chloride presented a regular spherical shape. When calcium chloride was added at a concentration of 0.15 mg/ml, the particle morphology was altered by aggregation. The samples synthesized with 0.29 mg/ml calcium chloride presented more regular "donut" shapes and less aggregation as compared with the samples with 0.15 mg/ml, but with larger particle sizes. The addition of calcium chloride may explain the high polydispersity indexes observed. For example, the sample with 0.15 mg/ml calcium chloride presented a high PI (0.480) due to aggregation of smaller particles. The samples synthesized with 0.29 mg/ml calcium chloride showed a PI of 0.55, with a mixture of larger and smaller particles, but with substantially less aggregation. We hypothesize that, at the higher calcium concentrations, the lecithin layers from different particles may fuse with one another, leading to fewer but larger particles.

EXAMPLE 9

Stability Measurements. The liquid aqueous suspension of the β-carotene nanoparticles was stable at temperatures up to 100° C. Observations out to several weeks at room temperature did not show any visible phase separation, nor any significant change in color. A liquid sample of the suspension was centrifuged at 10,000 rpm for 15 minutes without leakage, and without any visible phase separation of β-carotene. A nanoparticle powder prepared by lyophilization presented a uniform color distribution upon re-suspension in water, without any visible phase separation.

EXAMPLE 10

Effect of pH. The effect of pH was analyzed by titration with HCl and NaOH to each of several pH values, and then measuring particle size and zeta potential. The results suggested that the system was stable at pH higher than about 3 (data not shown).

EXAMPLE 11

Alternative colorants that may be used in practicing the present invention. Natural sources produce numerous pigments that may be incorporated into nanoparticles in accordance with the present invention. Fruits, vegetables, insects, microalgaes, and fungi are examples of natural sources for natural pigments. Among the families of pigments are carotenoids, anthocyanins, betalains, polyphenols, chlorophylls, and monascus. The following Table sets forth a number of commonly-used natural colorants.

| Colorant | Color | Common Source(s) | Comments |
| --- | --- | --- | --- |
| Curcumin | Yellow, bright lemon | Turmeric | Light sensitive, low water solubility |
| Lutein | Golden yellow | Alfalfa | Poor stability to light, heat, acid, oxidation, and $SO_2$. Fades in the presence of ascorbic acid. |

| Colorant | Color | Common Source(s) | Comments |
|---|---|---|---|
| Carotenes or natural mixed carotenes | Yellow to orange | Palm oil, algae | Insoluble in water below pH 5 |
| Bixin/Norbixin | Orange | *Bixa orellana* | Good stability to light, heat, and acid. Stable to ascorbic acid in soft drinks. |
| Capsanthin/ capsorubin | Reddish orange | Paprika | Fair stability to light and heat |
| Lycopene | Orange to red | Tomatoes | Excellent stability to light, heat, and acid. Fades in the presence of ascorbic acid or $SO_2$. Not allowed as a colorant in the U.S. |
| Carmine, carminic acid | Pink to red | Conchineal insects | Good stability to light, heat, and acid. Water soluble. Fades in the presence of ascorbic acid or $SO_2$ |
| Chlorophyll | Olive green | Lucerne, nettle | Liposoluble. Not allowed as a colorant in the U.S. |
| Copper or sodium chlorophyll | Bluish green | Lucerne, nettle | More stable than chlorophylls. Saponification can make it water-soluble. |
| Carbon black | Grey to black | Vegetable material | Very fine powder. Not lipid or water soluble. Not allowed as a colorant in the U.S. |
| Titanium dioxide | White | Anatase | |

(Table adapted from A. Downham et al. (2000))

Examples of alternative carotenoids that may be used as colorants in this invention include the following: α-carotene, β-carotene, zeacarotenes, lycopene, astaxanthin, canthaxanthin, zeaxanthin, capsanthin, capsorubin, violaxanthin, antheraxanthin, lutein. Examples of other colorants include betacyanins (e.g., betanidin, betanin), gardenia (e.g., geniposide, genipin), and monascus (e.g., monascin, ankaflavin).

EXAMPLE 12

Alternative polymers that may be used in practicing the present invention. Examples of alternative polymers that may be used in this invention include the following: pectins, starches, gelatins, starch derivatives, dextrin, xanthan gum, gum Arabic, guar gum, alginates, carrageenan, galactomannans, milk proteins, chitosan, inulin, konjac mannan. These polymers have been used in the food industry for purposes such as thickening, thinning, coating, gelling agents, or fat replacement. In general, these polymers are soluble in water, swell in water, and have properties that vary as a function of chemical structure and environmental conditions.

Starches. Maize, potato, and rice are the most important commercial sources of starch. Starch is a compact, semi-crystalline granule with size range of 1 to 100 μm, which can contain linear or branched (amylose or amylopectin) building blocks. Amylose usually forms one of three types of crystals depending on its source (A: cereals, B: tuber, and C: pea and bean varieties), and the degree of hydration. The number of glucose units per starch molecule can range from 500 to more than 6000. A branched amylopectin may contain 30 units of glucose per branch, but its molecular weight can be 1000 times higher than that of amylose (up to ~400 million). When the temperature increases, the starch chains begin to come apart due to swelling in water, which results in some degree of granule rupture, and an increase in the solution viscosity.

Carrageenan. Different types of Rhodophycae, so-called "red seaweeds," are used to obtain carrageenan, a polysaccharide that is commonly used as a viscous thickener. The rheological properties of the gels can vary as a function of the type of carrageenan used. Kappa, iota, and lambda carrageenans are common types, extracted from *Euchema cottoni*, *E. spinosum*, and *Gigartina* spp., respectively. This polysaccharide has sulfate- and non-sulfate-containing units of galactose and 3,6-anhydrogalactose, linked by alternating α-1,3 and β-1,4 glycosidic links. The molecular weight of carrageenan typically ranges from ~400 kDa to ~600 kDa. The main differences among carrageenans arise from differing amounts of ester sulfate and 3,6-anhydrogalactose units, characteristics that affect gel strength, texture, hydration, melting temperature, and other properties. Carrageenans are generally soluble in hot water; the lambda, kappa, and iota types are also soluble in cold water. Carrageenans hydrate more at higher temperatures, and typically set at temperatures of ~40 to ~60° C., depending also on the concentrations of cations. The pH affects gel stability.

Agar. Agar is a hydrocolloid extracted from groups of purple-red marine algae. Agar comprises two principal components, agaropectins and agaroses, whose proportions vary as a function of algal species and extraction process. The gelling component of agar is agarobiose. Typical molecular weight is $10^5$ g/mol, with low sulfate content (~0.15%). Gels formed by agaroses are based on hydrogen bonding ("physical" gels). Typical gelling temperature is around 38° C., and typical melting temperature is around 85° C.

Xanthan gum. Xanthan gum is an extracellular, cold water-soluble polysaccharide produced by *Xanthomonas campestris*. Its commercial production is based on an aerobic submerged fermentation, and xanthan gum is recovered by precipitation with isopropyl alcohol. Xanthan gum has a β-D-glucose linear backbone, with trisaccharide side chains. The branches contain glucuronic acid linked to two mannoses. The terminal mannose is pyruvated (50%), and the non-terminal mannose carries an acetyl group at C-6. In solution the side chains wrap around the backbone which protects the labile β-(1-4) linkage. Solutions of xanthan gum exhibit pseudoplastic behavior (an increase in shear stress progressively reduces viscosity), with good stability to changes in pH and temperature, and resistance to enzymatic degradation.

Gum Arabic. Gum Arabic is a complex combination of polysaccharides, arabinogalactan oligosaccharides, and glycoproteins. The ratio of L-arabinose to D-galactose may vary. The molecular weight of the polysaccharides making up gum Arabic is around $2.5 \times 10^6$ g/mol, and the molecular weight of the glycoproteins is around $2.5 \times 10^6$ g/mol. Gum Arabic is extracted from exudates found in the branches and stems of two species of acacia tree in sub-Saharan Africa. The molecular structure is highly compact and branched. It can act as an emulsifier due to the presence of hydrophobic polypeptide chains and carbohydrate blocks; the latter also inhibit flocculation and coalescence through electrostatic and steric repulsion.

Pectin. Pectin is a natural polysaccharide formed from polygalacturonic acid and rhamnose. The backbone of pectin comprises poly-(1-4)-α-D-galacturonic acids and sugars that are neutral in pH. There are also neutral side chains from the galacturonic acid units, side chains containing arabinose and galactose units. The acid groups of galacturonic acid are partially esterified with methanol, and some hydroxyl groups may be acetylated. Apple and citrus pectin have a lower degree of acetylation than beet pectin. Lower molecular weight pectins ($\sim 5*10^4$ g/mol) tend to be more rigid, and to have a more extended conformation. Pectins with a lower concentration of methoxyl groups form thermo-reversible gels when exposed to calcium ions at a low pH (~3.0-4.0). Pectins with a higher concentration of methoxyl groups form gels in the presence of sugars at low pH, and the acid groups are not completely ionized. The rate of cooling affects gelation, with rapid cooling producing thicker gels.

Alginate. Alginate is a block copolymer naturally produced by brown algae. There are several varieties commercially used, derived primarily from *Laminaria japonica*, *Laminaria digitata*, and *Laminaria hyperborean*. The polymers contains random mixtures of guluronate and mannuronate. The alginates from different *Laminaria* species typically contain different ratios of guluronate and mannuronate, and therefore have different properties. The solubility of alginate in water is affected by pH, ionic strength, and the type of ions present in the water. Treatment with HCl during extraction produces alginic acid. An abrupt decrease in pH causes precipitation of alginic acid, while a slower release of protons results in the formation of an alginic acid gel. The composition of the alginate also affects its behavior at low pH. As a rule, increasing the disorder of the polymer chain inhibits the formation of crystalline regions, and precipitation can occur at a pH as low as 1.4. The ionic strength affects polymer chain extension and thus solution viscosity. For example, a high concentration of potassium chloride can precipitate and fractionate alginates having high mannuronate content. Alginate should be fully hydrated in pure water under shear before high concentrations of salts are dissolved in the same solution. The viscosity of an alginate solution can be rapidly reduced by degradation; for example the glycosidic linkages are susceptible to both acid and alkaline degradation, oxidation by free radicals, and enzymatic hydrolysis. Gel properties are not strongly temperature-dependent; alginate gels are generally considered heat-stable.

Chitosan. Chitosan is a hydrophilic polysaccharide resulting from the N-deacetylation of chitin. Chitosan is a linear polysaccharide comprising randomly distributed β-(1-4)-linked D-glucosamine (deacetylated units) and N-acetyl-D-glucosamine (acetylated units). Typical molecular weights are $10^4$-$10^5$ g/mol. Generally, chitosans have nitrogen content above ~7% and a degree of acetylation below ~0.4. Chitosan is insoluble in most organic solvents, and is insoluble in aqueous solutions at pH above ~6. Chitosan is soluble in acidic aqueous solutions, in which it becomes polycationic.

Other hydrocolloid-forming polymers. The polymer used in this invention may alternatively be selected from other polymers known in the art, for example other polymers that are used in the food industry, and that are typically employed for forming hydrocolloids, such as inulin, Konjac mannan, tragacanth, karaya, xyloglucan, curdlan, cereal β-glucans, and galactomannans. It is preferred that the polymer be one that is readily crosslinkable.

EXAMPLE 13

Alternative surfactants that may be used in practicing the present invention. Examples of alternative surfactants that may be used in this invention include the following, as well as others known in the art: glycerine fatty acid esters, acetylated monoglyceride, lactylated monoglyceride, citric acid esters of monoglycerides, succinic acid esters of monoglycerides, diacetyl tartaric acid esters of monoglycerides, polyglycerol esters of fatty acids, polyglycerol polyricinoleate, sorbitan esters of fatty acids, propylene glycol esters of fatty acids (PG ester), sucrose esters of fatty acids, calcium stearoyl-2-lactate, lecithin, and their respective derivatives.

EXAMPLE 14

Alternative cross-linking agents that may be used in practicing the present invention. Examples of alternative cross-linking agents that may be used in this invention include the following: calcium, magnesium, and other cross-linking agents that are known in the art for cross-linking the particular polymer(s) used. Other examples include other divalent and trivalent cations known in the art, including barium, aluminum, manganese, and organic di-ammonium ions.

EXAMPLE 15

Layer-by-layer assembly. In an alternative embodiment, the nanoparticles may be prepared via layer-by-layer (LBL) assembly, using two or more alternating layers of opposite charge. In one example, beta-carotene is entrapped in a lecithin-stabilized emulsion, and surrounded by an intermediate layer of chitosan (positively-charged), and a pectin (negatively-charged) outer layer. Examples of other negatively-charged polymers include carrageenan, xanthan gum, and gellan gum. The use of an organic solvent, such as ethyl acetate, should help produce smaller particle sizes than have been produced by previous layer-by-layer techniques. To the inventors' knowledge, prior layer-by-layer techniques have most commonly reported particle sizes around 1000, with some down to 450 nm, or down to 250 nm when sonication is employed. By contrast, the present technique can make LBL particles at least as small as 150 nm, and possibly smaller.

A buffer solution is prepared by adding acetic acid to 60 mL of water until the pH reaches 4. The pH should be 4 or slightly higher, to keep the pectin negatively charged. This buffer solution is then separated into three separate portions of 20 mL each. Ethyl acetate (1.85 mL) is added to buffers 1 and 2, but not to buffer 3. Lecithin (0.24 g) is dissolved in buffer 1. Chitosan (0.007 g) is dissolved in buffer 2 with mixing. If the chitosan does not dissolve initially, HCl or acetic acid is added slowly until the chitosan becomes soluble. Pectin (0.013 g) is dissolved in buffer 3. A fourth solution is formed by dissolving 0.0031 g beta carotene in 6 mL ethyl acetate.

The beta carotene solution is slowly added to the lecithin solution with a syringe, with homogenization at 14,000 rpm in a high-speed blender; and the resulting primary emulsion is further homogenized for five minutes. Next, the emulsion is sonicated for ten minutes at 38% amplitude, to reduce emulsion droplet size and to break up droplet aggregates. During sonication, the emulsion is placed in an ice bath to prevent excess heat buildup. Then the chitosan solution is added to the primary emulsion with a syringe to form a secondary emulsion. The secondary emulsion is also homogenized in a high-speed blender at 14,000 rpm for five minutes, and sonicated for thirty seconds in an ice bath at 38% amplitude to inhibit droplet aggregation. Next, ethyl acetate is evaporated by placing the secondary emulsion in a round bottom flask connected to a Rotovap™ reduced pressure evaporator, operating at 50 mmHg pressure in a 33° C. water bath for ten minutes.

After the ethyl acetate is evaporated, the pH is tested to ensure that the pH is 4 or higher prior to the addition of pectin; if appropriate, the pH is adjusted. Then the pectin solution is added to the secondary emulsion with a syringe while homogenizing at 14,000 rpm for five minutes with a high-speed blender, followed by sonication for thirty seconds in an ice bath to inhibit droplet aggregation. To optionally freeze-dry the resulting tertiary emulsion, trehalose (1:1 w/w) or other cryoprotectant should be added to protect the particle structure during freezing. After the addition of trehalose, the solution is frozen and held at −80° C. for one hour, followed by freeze-drying at −40° C. and 0.06 millibar pressure for ten hours. Other cryoprotectants known in the art may also be used, such as sucrose, or amino acids, for example lysine, arginine, and histidine.

The resulting particles will be measured and tested as before. Preliminary results have suggested, subject to confirmation in follow-up experiments, that the above protocol will produce a stabilized emulsion, with beta-carotene entrapped in nanoparticle covered by layers of chitosan and pectin, with particle diameters averaging around 150 nm, and a zeta potential around −32 mV (data not shown).

Miscellaneous, and Definitions

In the specification and claims, unless context clearly indicates otherwise, the terms "regions," "core," "layers," and similar terms should be understood to refer to concentric regions of a particle that are generally distinct from one another, and that have generally differing compositions. It will be understood by those of skill in the art that some intermingling of the components of different regions may occur, and that boundaries between adjacent regions will not necessarily be sharply defined.

In the specification and claims, unless context clearly indicates otherwise, the terms "primarily," "most," and similar terms should be understood to mean more than half (>50%), as determined by mass (or, equivalently, as determined by weight).

In the specification and claims, unless context clearly indicates otherwise, the "diameter" of a particle, core, or layer refers to the largest dimension across the particle, core, or layer. Note that the use of the term "diameter" does not necessarily imply that the particle, core, or layer has a spherical shape or a circular cross-section.

In the specification and claims, unless context clearly indicates otherwise, the "thickness" of a particle, core, or layer refers to the average distance to traverse the particle, the core, or a section of a layer. For example, if a layer is a shell with a uniformly spherical, concentric shape, then the thickness of the layer is the difference between the radius of the outer sphere and the radius of the inner sphere bounding the layer. Note also that this definition and the preceding definition necessarily imply that the "thickness" of a particle, core, or layer will never exceed its "diameter."

In the specification and claims, unless context clearly indicates otherwise, in a case where the boundaries of a region are not sharply defined, the "diameter" or the "thickness" of a core or a layer that primarily comprises one or more specified compounds refers to the diameter or thickness of the region within which the specified one or more compounds comprise more than half (>50%) of the material, as determined by mass (or, equivalently, as determined by weight). The diameter and thickness, or the mean diameter and thickness, may be measured by any of several means known in the art, including among others dynamic light scattering, transmission electron microscopy, and scanning electron microscopy, with dynamic light scattering generally being preferred. In preferred embodiments, the hydrophobic cores in the particles have a mean diameter of about 20 nm or greater, preferably about 50 nm or greater, more preferably about 100 nm or greater. In preferred embodiments, the hydrophobic cores in the particles have a mean diameter of about 3 µm or smaller, preferably about 1 µm or smaller, more preferably about 500 nm or smaller.

In the specification and claims, unless context clearly indicates otherwise, nanoparticles are considered to be "water-soluble" either if the nanoparticles will dissolve in water; or if the nanoparticles will form a uniform colloid or suspension in water such that, if the colloid or suspension is allowed to stand undisturbed at room temperature, without mixing, for a period of seven days, there will be no substantial settling of the nanoparticles from the aqueous phase, nor any substantial phase separation of the nonpolar colorant or other nonpolar compound from the aqueous phase. In other words, "water soluble" is used here in a pragmatic sense, and need not necessarily imply that the nanoparticles form an aqueous "solution" within the technical meaning of "solution" as one might find in a chemistry textbook.

The present invention is particular suited for use with compounds that are only slightly soluble or insoluble in water. In many circumstances, it will be unnecessary to draw a sharp distinction between compounds that are "water-soluble," those that are "slightly soluble," and those that are "insoluble" in water. In many circumstances, these distinctions are pragmatic ones, based on whether a compound is, or is not sufficiently soluble in water to serve the particular function desired by the user. In other circumstances, if a more mathematically precise distinction is needed, then a compound might be said to be "slightly soluble" in water if, at 25° C., its solubility is less than about 5% (w/v); or to be "insoluble" in water if, at 25° C., its solubility is less than about 1% (w/v).

The complete disclosures of all references cited in this specification are hereby incorporated by reference. In the event of an otherwise irreconcilable conflict, the present specification shall control.

What is claimed:

1. A plurality of nanoparticles; wherein each said nanoparticle comprises one or more hydrophobic cores, a surfactant intermediate layer, and a polymeric layer; wherein each of said one or more hydrophobic cores is bound to said surfactant intermediate layer via nonpolar-nonpolar intermolecular interactions; and said surfactant intermediate layer is bound to said polymeric layer via electrostatic or polar interactions; and wherein:

(a) each of said one or more hydrophobic cores comprises primarily one or more hydrophobic compounds; and the mean diameter of said cores is at least about 20 nm; and (b) said surfactant intermediate layer comprises primarily one or more surfactant compounds; wherein each of said one or more surfactant compounds comprises one or more hydrophobic moieties and one or more hydrophilic moieties; wherein said surfactant hydrophobic moieties orient preferentially toward said one or more hydrophobic cores, and bind said one or more hydrophobic cores via nonpolar-nonpolar intermolecular interactions; and wherein said surfactant hydrophilic moieties orient preferentially away from said one or more hydrophobic cores; and (c) said polymeric layer comprises alginic acid, which alginic acid comprises hydrophilic moieties; wherein some of said alginic acid hydrophilic moieties orient toward said surfactant intermediate layer, and bind said surfactant intermediate layer via electrostatic or polar interactions between said alginic acid hydrophilic moieties and said surfactant hydrophilic moieties; and wherein some of said alginic acid hydrophilic moieties orient outward, so that said alginic acid hydrophilic moieties are favorably positioned to be able to interact with water molecules via electrostatic or polar intermolecular interactions;

(d) said polymeric layer additionally comprises one or more crosslinking moieties that crosslink at least some of said alginic acid molecules to one another, and that enhance the structural integrity of said nanoparticle as compared to an otherwise identical nanoparticle lacking said one or more crosslinking moieties; wherein said one or more crosslinking moieties comprise calcium cations;

(e) said nanoparticles are water-soluble; such that the total concentration of said one or more hydrophobic compounds that is soluble in water, when said one or more hydrophobic compounds are present as a component of said nanoparticles, is substantially greater than the total concentration of said one or more hydrophobic compounds that is soluble in water lacking surfactant, at the same temperature and pressure, when said one or more hydrophobic compounds remain unmodified and are not incorporated into such nanoparticles;

(f) said nanoparticles have the property that, if said nanoparticles are dissolved in water and the resulting solution is allowed to stand undisturbed at room temperature without mixing, for seven days, then there will be no substantial settling of said nanoparticles from the aqueous phase, nor any substantial phase separation of said one or more hydrophobic compounds; and said nanoparticles have the further property that, if said nanoparticles are dissolved in water and the resulting mixture is centrifuged at 10,000 rpm for 15 minutes, there will be no leakage of said one or more hydrophobic compounds from said nanoparticles, nor any substantial phase separation of said one or more hydrophobic compounds; and (g) the mean diameter of said nanoparticles is less than about 5 μm.

2. A plurality of nanoparticles as recited in claim 1, wherein the mean diameter of said hydrophobic cores is at least about 50 nm.

3. A plurality of nanoparticles as recited in claim 1, wherein the mean diameter of said hydrophobic cores is at least about 100 nm.

4. A plurality of nanoparticles as recited in claim 1, wherein the mean diameter of said hydrophobic cores is less than about 3 μm.

5. A plurality of nanoparticles as recited in claim 1, wherein the mean diameter of said hydrophobic cores is less than about 1 μm.

6. A plurality of nanoparticles as recited in claim 1, wherein the mean diameter of said hydrophobic cores is less than about 500 nm.

7. A plurality of nanoparticles as recited in claim 1, wherein the thickness of said polymeric layer is between about 50 nm and about 1 μm.

8. A plurality of nanoparticles as recited in claim 1, wherein the thickness of said surfactant intermediate layer is between about 1 nm and about 10 nm.

9. A plurality of nanoparticles as recited in claim 1, wherein the weight of said one or more hydrophobic compounds is between about 0.1% and about 10% of the total weight of said nanoparticles.

10. A plurality of nanoparticles as recited in claim 1, wherein the weight of said one or more hydrophobic compounds is between about 10% and about 20% of the total weight of said nanoparticles.

11. A plurality of nanoparticles as recited in claim 1, wherein said one or more hydrophobic compounds comprise one or more natural colorants.

12. A plurality of nanoparticles as recited in claim 1, wherein said one or more hydrophobic compounds comprise primarily β-carotene.

13. A plurality of nanoparticles as recited in claim 1, wherein said one or more hydrophobic compounds comprise primarily β-carotene; and wherein said one or more surfactant compounds comprise primarily lecithin.

14. A plurality of nanoparticles as recited in claim 1, wherein one or more moieties additionally link at least some of said alginic acid molecules to at least some of said surfactant molecules.

15. A plurality of nanoparticles as recited in claim 1, wherein the mean diameter of said nanoparticles is between about 120 nm and about 950 nm.

16. An aqueous solution of a plurality of nanoparticles as recited in claim 1.

17. A process for synthesizing a plurality of nanoparticles as recited in claim 1; said process comprising the steps of:

(a) dissolving one or more hydrophobic compounds in a nonpolar solvent;

(b) forming an emulsion of droplets comprising water, one or more surfactants, the one or more hydrophobic compounds, and the nonpolar solvent;

(c) reducing the average size of the droplets by sonicating or microfluidizing the emulsion;

(d) stabilizing the droplets by binding to them a layer comprising alginic acid, and crosslinking the alginic acid molecules to one another with calcium cations; and (e) evaporating the nonpolar solvent; wherein steps (d) and (e) may be conducted in either order, or simultaneously.

18. A process as recited in claim 17, wherein said stabilizing step additionally comprises linking the alginic acid molecules to the surfactant molecules.

* * * * *